(12) United States Patent
Eklund et al.

(10) Patent No.: US 6,889,691 B2
(45) Date of Patent: May 10, 2005

(54) AUTO CPAP

(75) Inventors: Ove Eklund, Surrey (GB); Henrik Bergfalk, Göteborg (SE); Jan Anders Hedner, Göteborg (SE); Hans Petter Knagenhjelm, Pixbo (SE)

(73) Assignee: Breas Medical AB (SE)

( * ) Notice: Subject to any disclaimer, the term of this patent is extended or adjusted under 35 U.S.C. 154(b) by 311 days.

(21) Appl. No.: 09/965,681

(22) Filed: Sep. 27, 2001

(65) Prior Publication Data
US 2003/0000528 A1 Jan. 2, 2003

(30) Foreign Application Priority Data
Oct. 2, 2000 (SE) .............................................. 0003531

(51) Int. Cl.[7] ............................................ A61M 15/00
(52) U.S. Cl. ........................... 128/204.21; 128/200.24; 128/204.23
(58) Field of Search ..................... 128/200.24, 204.18, 128/204.21, 204.23

(56) References Cited

U.S. PATENT DOCUMENTS

| | | | |
|---|---|---|---|
| 3,850,168 A | 11/1974 | Ferguson et al. | 128/146.7 |
| 5,058,600 A | 10/1991 | Schechter et al. | 128/716 |
| 5,092,343 A | 3/1992 | Spitzer et al. | 128/733 |
| 5,134,995 A | 8/1992 | Gruenke et al. | 128/204.23 |
| 5,146,918 A | 9/1992 | Kallok et al. | 128/419 G |
| 5,251,626 A | 10/1993 | Nickolls et al. | 607/14 |
| 5,309,921 A * | 5/1994 | Kisner et al. | 600/532 |
| 5,458,137 A | 10/1995 | Axe et al. | 128/204.23 |
| 5,503,161 A | 4/1996 | Van Den Heuvel | 128/773 |
| 5,584,291 A | 12/1996 | Vapola et al. | 128/630 |
| 5,666,466 A * | 9/1997 | Lin et al. | 704/246 |
| 5,953,713 A | 9/1999 | Behbehani et al. | 706/16 |
| 5,999,846 A * | 12/1999 | Pardey et al. | 600/544 |
| 6,290,654 B1 * | 9/2001 | Karakasoglu | 600/529 |

FOREIGN PATENT DOCUMENTS

| | | | |
|---|---|---|---|
| EP | 1 005 829 A1 | 7/2000 | A61B/5/087 |
| WO | WO 00/19895 | 4/2000 | A61B/5/08 |
| WO | WO 0100264 A1 | 1/2001 | A61M/16/00 |

OTHER PUBLICATIONS

IEEE Transactions on Systems, Man, and Cybernetics–Part B: Cybernetics, vol. 27, No. 1, Feb. 1997, Quen–Zong Wu et al.: "On–Line Signature Verification Using LPC Cepstrum and Neural Networks," abstract.

IEEE Transactions on Biomedical Engineering, vol. 45, No. 11, Nov. 1998, J. Bock et al., "Toward Prediction of Physiological State Signals in Sleep Apnea," abstract.

Neural Network Based Multi Sensor Heart Sound Analysis, Barschodorff, et al., 1991 IEEE, pp. 303–306.

Snore Detection Using a Neural Network, Masters Thesis by Francisco Javier Lopez, presented to the Faculty of the Graduate School of The University of Texas at Arlington.

(Continued)

Primary Examiner—Aaron J. Lewis
(74) Attorney, Agent, or Firm—Moser, Patterson & Sheridan

(57) ABSTRACT

A method for the detection and treatment of disordered breathing during sleep employs an artificial neural network (ANN) in which data related to breathing gas flow are analyzed. A respiratory circuit is established by connecting the patient to a continuous positive airway pressure (CPAP) system with pressurized breathing gas supply, the gas flow in the circuit is periodically sampled, one or several cepstrum parameters distinctive of various breathing patterns are periodically calculated; the parameter values are periodically fed to an ANN trained to recognize breathing patterns characteristic of sleep disordered breathing and are analyzed in the network, the CPAP pressurized breathing gas supply is controlled in response to the ANN output. Also disclosed is a corresponding apparatus.

31 Claims, 2 Drawing Sheets

OTHER PUBLICATIONS

T. Kohonen, et al., "Phonetic Typewriter for Finnish and Japanese," Proc IEEE ICASSP, NY, NY 1988.

Leung et al., "Some Phonetic Recognition Experiments Using Artificial Neural Nets," Proc IEEE ICASSP, NY, NY 1988.

P. Brauer, "Infrastructure in Kohonen Maps," Proc. IEEE ICASSP, Glasgow, Scotland, 1989.

P. Knagenhjelm, "A Recursive Design Method for Robust Vector Quantization," Proc. ICSPAT, Boston, MA 1992.

Wu, Quen–Zong et al.: "On–line Signature Verification Using LPCC Cepstrum and Neural Networks." IEEE Transactions on Systems, Man, and Cybernetics–Part B: Cybernetics, Feb. 1997, vol. 27, No. 1, abstract.

Bock, Joel et al.: "toward Prediction of Physiological State Signals in Sleep Apnea." IEEE Transactions on Biomedical Engineering, Nov. 1998, vol. 45, No. 11, abstract.

* cited by examiner

AUTO CPAP

CROSS REFERENCE TO RELATED APPLICATIONS

The present application claims the benefit of Swedish patent application No. SE 0003531-1 which was filed on Oct. 2, 2000 and is incorporated herein by reference.

FIELD OF THE INVENTION

The present invention relates to method and an apparatus for the detection and treatment of disordered breathing during sleep, in particular to a method and apparatus employing an artificial neural network.

BACKGROUND OF THE INVENTION

U.S. Pat. No. 5,953,713 (Behbehani et al.), incorporated herein by reference, discloses a method for treating sleep disordered breathing comprising measuring a respiration-related variable at an interface placed over a patient's airway coupled to a pressurized gas, feeding cepstrum data obtained from the respiration related variable(s) into an artificial neural network trained to recognize patterns characterizing sleep disordered breathing; supplying pressurized gas to the patients airway in response to recognition of the artificial neural network of sleep disordered breathing. The sampling frequency of the pressure transducer's output disclosed in the preferred embodiment is 512 Hz. A Fourier transform is calculated every $1/16$ second using a 32 sample values window.

Another aspect of frequency analysis is that, on the one hand, the precision is proportional to the number of input data but that, on the other hand, the response time is correspondingly increased. While high precision is welcome since rather small changes in breath pattern can be detected, a slower response increases the risk of progressive deterioration of the airway aperture, and thereby more severe respiratory disturbance before the patient is aroused. Other methods of detecting sleep disorder are based on breath-by-breath analysis.

Alternatively, if adequate treatment is not installed, the patient will be aroused in a more extended time perspective.

OBJECTS OF THE INVENTION

It is an object of the present invention to provide an improved method for automatically supplying continuous positive airways pressure to a patient.

It is another object of the present invention to provide an automatic continuous positive airways pressure apparatus (ACPAP) which lacks at least some of the drawbacks of state-of-the-art apparatus.

Additional objects of the invention are evident from the following short description of the invention, the attached drawings illustrating a preferred embodiment, the detailed description thereof, and the appended claims.

SUMMARY OF THE INVENTION

The present invention is based on the insight that a direct analysis of the flow signal is more specific than an analysis of disordered breath, in particular flow limited breath, based on frequency analysis.

According to the present invention is provided an automatic continuous positive airways pressure apparatus (ACPAP) in which the air flow from a CPAP or other system providing positive air pressure to a patient is measured for calculation of a number of parameters specific to the signal. The set of parameters comprises cepstrum coefficients and energy content, and is selected to indicate an apneic event of breathing during sleep, such as apnea, hypoapnea, and flow limitation. Data for these parameters collected from a large number of patients were used to train an artificial neural network to teach the system the variation ranges of the parameters for subsets of patients under a number of circumstances. The result from the artificial neural network is obtained as a low-dimensional grid of nodes in which each respiration type is represented by trajectory or a subsets of nodes. A trajectory for a normal breath looks very different from that of a breath during disturbed sleep.

If breathes symptomatic of a condition of disturbed sleep are detected the CPAP pressure is increased. In contrast, CPAP pressure is reduced in a normal condition.

Thus, according to the present invention is disclosed a method for the detection and treatment of disordered breathing during sleep employing an artificial neural network in which data related to breathing gas flow are analyzed in an artificial neural network.

Specifically, a method according to an embodiment of the present invention comprises the following steps:

placing a mask with a tube over a patient's airway, the mask being in communication with a source of a pressurized breathing gas controlled by a CPAP, thereby establishing a respiratory circuit;

periodically sampling the gas flow in the circuit;

periodically calculating values for one or several parameters distinctive of a breathing pattern;

periodically feeding the parameter values to an artificial neural network trained to recognize breathing patterns characteristic of sleep disordered breathing;

analyzing the parameter values in the neural network;

controlling pressurized breathing gas supply in response to the output from the neural network.

It is preferred to feed said parameter values to the network at a frequency of from 2 Hz to 30 Hz, preferably of about 20 Hz. It is preferred for said parameters to comprise cepstrum coefficients and energy slope.

According to a first preferred aspect of the invention the artificial neural network is trained with data collected from a large number of patients. The data will have been collected from patients differing in many aspects: sex, age, body weight, breath pattern, etc. In addition, variants of sleep disordered breathing such as those occurring preferentially in the back position, those occurring during particular stages of sleep, and those occurring under the influence of drugs or alcohol need to be addressed.

Such data are advantageously collected in sleep laboratories in which the state of sleep is followed as well as the type and severity of the breathing disturbance is monitored by use of a polysomnography system. The collected data form a primary database. During the training of the artificial neural network the data is quantified under formation of a small secondary dedicated database which can be stored in a ACPAP. Thus, according to the present invention, a dedicated secondary database obtained from a primary database comprising data collected from a large number of persons is stored in the ACPAP.

According to a second aspect of the invention it is preferred to periodically sample the gas flow during breathing.

The ANN comprises a number of nodes representing sets of training data. Each note reflects a state or an incident (feature). Neighboring nodes represent incidents of small geometric distance. In the same way as in training an incident vector is extracted for each flow data sample. The Euclidean distance from the incident vector to each node is calculated. The node in closest proximity to the vector is associated with it. Sequences of incident vectors are followed as sequences of nodes in the artificial neural network. It can be said that a sequence of nodes is the response of the network. Thus a trajectory in the geometric structure of the network (response) is followed rather than in the parameter space. The fact that the dimension of the network most often is smaller than the parameter space is of advantage since calculation thereby is simplified. The response from the network forms the basis for distinguishing between apnea, hypoapnea and a normal breathing state and thus, for CPAP pressure control.

The invention thus is based on the use of an artificial neural network (ANN) of Kohonen-map type (associative memory; T. Kohonen, Self-Organization and Associative Memory, $2^{nd}$ Ed., Springer Verl., Berlin 1987) for detecting apnea or apnea-like episodes. The ANN is trained with data obtained from a number of patients in a sleep laboratory. The readily trained ANN forms a global (universal) structure of data stored in a non-volatile memory in an ACPAP. In use the breathing pattern of a patient forms trajectories (traces) in the ANN. A normal breathing cycle forms a closed trajectory. A trajectory deviating from normal is indicative of a breath disturbance. The ANN is structured in way so as to make certain areas represent initial stages of apnea. The passage of a trajectory through such an area or touching its border indicates that the amount of air provided to the patient should be increased so as to re-establish normal breathing. Once breathing has been normalized the adduced amount of air is reduced to normal, i.e., to the pre-established base value.

The artificial neural network is trained in two phases described in P. Brauer and P. Knagenhjelm, Infrastructure in Kohonen Maps, Proc. IEEE ICASSP, Glasgow 1989.

The purpose of the analysis is to extract, from the series of air flow rate measurements, values of the parameters chosen to classify and detect apneic and hypoapneic states. In each single analysis the parameters are made to form an incident or feature vector on which all training and decision-making is based. All sample values are individually analyzed in preparation for a quick response to changes in flow which are typical forewarnings of an apneic or hypoapneic state.

According to a third preferred aspect of the invention linear predictive coding is used to analyze the parameter values fed to the neural network. A linear predictive coding analysis comprising four parameters is carried out for all samples. In particular, the so-called A-parameters from the analysis are converted to cepstrum parameters for optimal correlation between parameter distance and conceptual distance, that is, so-called associativity.

According to a fourth preferred aspect of the invention the prediction error in calculating linear predictive coding is used as a basis for the parameter next in line. The error is filtered to counteract short-term variations and normalized with the total energy of the analytical window.

For calculations of energy a larger window than for the linear predictive coding analysis is used. The energy of the latest windows can be used to calculate a line the inclination which describes a trend. The difference in trend is used as a further parameter. Thus, according to a fifth preferred aspect of the invention, the inclination of a trend line calculated from measurements and is used as a parameter.

According to the present invention is also disclosed an apparatus for the detection and treatment of disordered breathing during sleep for use with a CPAP, the apparatus including a probe for sampling breathing air flow data, in particular on inhalation, and an artificial neural network for analyzing, directly or indirectly, said data to control breathing air pressure.

According to the present invention is also disclosed a CAPAP comprising a probe for sampling breathing air flow data, in particular on inhalation, and an artificial neural network for analyzing, directly or indirectly, said data to control breathing air pressure.

Further variations of the present invention are disclosed in the following detailed description of a preferred embodiment thereof illustrated in a drawing.

DESCRIPTION OF THE DRAWING

The invention is illustrated by a drawing comprising several figures, showing.

DESCRIPTION OF A PREFERRED EMBODIMENT

EXAMPLE 1

General

Figure 1:
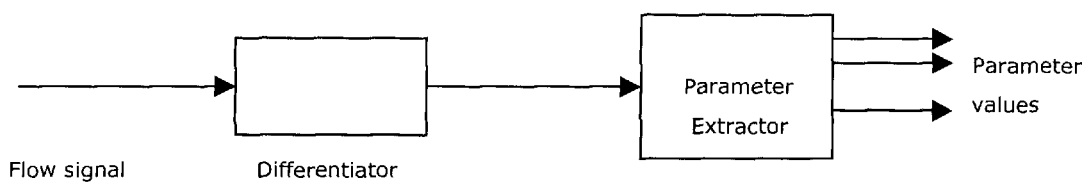
FIG. 1 depicts a block diagram regarding parameter extraction.

Primary Data Analysis. The purpose of the analysis is to extract, from the series of air flow rate measurements, values of the parameters chosen to classify and detect apneic and hypoapneic states. In each single analysis the parameters are made to form an incident or feature vector on which all training and decision-making is based. All sample values are individually analyzed in preparation for a quick response to changes in flow which are typical forewarnings of an apneic or hypoapneic state.

Incident Vector Parameters. LPC-Cepstrum. For each sample a Linear Predictive Coding (LPC) four-parameter analysis is carried out. The so-called A-parameters from the analysis are converted to cepstrum parameters for optimal correlation between parameter distance and conceptual distance, that is, associativity. The term cepstrum introduced by Bogert et al. in connection with echo time series analysis designates the inverse Fourier transform of the logarithm of the power spectrum of a signal. The transformation of a signal into its cepstrum is a homo-morphic transformation, see A. V. Oppenheim and R. W. Schafer, *Discrete-Time Signal Processing*, Prentice Hall, Englewood Cliffs, N.J., 1989. Residual. The error of prediction in calculating LPC is used as a basis for the following parameter. The error is filtered to oppose short-term variations, and is normalized with the total energy for the analytical window. Energy slope. For calculations of energy larger windows are used than for LPC analysis. The energy at the most recent windows is used to calculate a line the slope of which describes a trend. Difference in trend. The difference in trend is used as a further parameter.

Parameters. To detect an apneic event (i.e. central/obstructive apnea, hypoapnea, and flow limitations) a model is used to characterize typical qualities and features of the flow-signal during the event. The parameters of the model is chosen with the aim to be as distinct, unambiguous, and informative as possible. The set of parameters shall respond to typical apneic events that are readily detected by physicians. In addition to be sensitive to apneic events, it is important that the parameters shall be insensitive to features irrelevant to the task of detecting apneic events.

The Feature Vector. The values of the parameters are compiled to form a vector, below named the Feature Vector. Each time the flow-signal is measured (sampled), the values of the Feature Vector are extracted. This means that if the flow signal is measured $f_s$ times per second, and N parameter values are needed in the model, the data rate is increased from $f_s$ to $N \cdot f_s$ samples per second.

Prior to the extraction of parameter values, the flow signal is differentiated (high-pass filtered) to avoid the influence of the mean signal value. The mean will vary with patients and/or hardware and do not contribute in the classification of apneic events, and is therefore removed. Each N-dimensional Feature Vector can be regarded as one point in a N-dimensional signal space.

Training the Network. An Artificial Neural Network (ANN) is iteratively trained to organize groups or clusters of Feature Vectors with similar properties. The self organizing process known as Kohonen's Self-Organizing Feature Map [1-2] has shown great capability of performing this task.

The number of clusters is defined prior to the training and is determined by the required resolution of the ANN. The training is initiated by a set of M clusters, randomly positioned in the N-dimensional signal space.

The database used for training is formed by compiling the Feature Vectors from a large number of patients with various sleep disorders and at all stages of sleep. During the training, each input Feature Vector is compared to each cluster to find the one with best resemblance to the input vector. This cluster is voted winner, and is adjusted towards the input vector. In addition, all other clusters within a neighborhood to the winner in another domain, the so-called map-space are adjusted towards the input vector. The map-space is usually of low dimension containing one node for each cluster in the signal-space. The nodes are arranged in hexagonal or a square lattice, and the Euclidian distance between them defines their internal relation. A node's neighborhood is usually defined by a neighborhood function and contains the set all nodes in the beginning of the training whereas only a few (or none) are considered neighbors at the end. The further away a node is to the winner in the map-space, the less the corresponding cluster in the signal-space is adjusted towards the input vector. Thus all adjustments are done in the signal space, while the rules of adjustments are defined in the map-space.

The training time is predetermined, and an annealing function is used to "freeze" down the system causing only small adjustments at the end of the training. The neighborhood function creates correlation between the signal-space distance and the map-space distance allowing classification to be performed in the (low dimensional) map-space, rather than in the more complicated signal-space. The method described above is known as "unsupervised learning", i.e. there is no need to use classified data in the training procedure described above. Classification of data into various apneic events is a tedious task.

When the ANN is readily trained, the clusters will represent M features of the input flow signal including normal breathing, hypoapnea, flow-limitations, and apnea (provided these features are represented in the database used for training). The response of the ANN is proportional to the signal distance between the input signal and all the clusters. See FIG. 2. Often this output is of less interest in the case of classification. The output is instead used to find the node with best resemblance to a classified input, such as normal breathing and apneic events. This is known as the labeling phase in the design of the ANN. Classified Feature Vectors are presented for the ANN, the output is observed, and the node giving the highest output is labeled with the presented feature. The actual output thereafter is the label rather than the response value.

The set of clusters are now stored in the memory of the APAP to be used in runtime mode. Patient flow-data is analyzed exactly the same way as done in the training phase to extract the values of the parameters used in the model i.e. the Feature Vector. The vector is then presented to the network that will produce the output label (classification) which is used by the flow-control logic.

EXAMPLE 2

Algorithm

DATA ACQUISITION.

Let the flow signal be a digitized version of the analog flow-signal sampled at $f_s$ samples/second, giving a sequence of samples $$x_i, i=0,1, \ldots,$$

where $x_i$ is short for $x(i \cdot T)$ i.e. the sample at time instant $i \cdot T$ and $T=1/f_s$.

PREPROCESSING. To reduce the influence of individual patient variations and to facilitate classification stability, the signal should pass a device to remove the signal mean. Any kind of steep edge high pass filter can be employed, thus the ideal differentiator is used for simplicity. The output from the differentiator, d, (and the input to the parameter extractor) will then be $$d_i = x_i - x_{i-1} \text{ where } i=0,1, \ldots, \text{ and } x_{-1} \equiv 0$$

PREPROCESSING. The cepstrum coefficients have shown to well model the frequency content of the signal using only a few parameters (low order model). In addition, the dynamics of the cepstrum coefficients facilitate quantization of the parameters. Often the parameters are weighted to produce parameters with similar variances. The cepstrum coefficients are derivatives of the so called A-polynomial calculated by standard Linear Predictive Coding (LPC).

As the cepstrum coefficients used do not hold information about the signal energy, the cepstrum will be augmented with a parameter to account for the long term (say 10 seconds) energy variations. This parameter shall be insensitive to the absolute level of the flow signal and only reflect the relative fluctuations.

Cepstrum. To calculate P model parameters at time k, the last Wz input samples are used (windowing). The sample, $d_k$, is predicted to be $$\tilde{d}_k = -\sum_{l=1}^{P} a_l \cdot d_{k-l}.$$

Thus the prediction error signal is $$e_k = d_k - \tilde{d}_k = -\sum_{l=1}^{P} a_l \cdot d_{k-l}.$$

The task is to find the set, a, which minimizes the energy of the prediction error signal (i.e. finding the values of $a=[a_1, \ldots, a_p]$ to make $\tilde{d}_k$ as similar to $d_k$ as possible) over all samples within the window. The optimal solution is found solving the matrix equation $$R \cdot a = -r$$

known as the Yule-Walker or normal equation, using for instance the Cholesky algorithm.

The vector a constitutes the so called A-polynomial which is transformed into a set of cepstrum coefficients c using the following algorithm:

$$c_0 = 0$$

$$c_1 = a_1$$

$$c_n = a_n - \sum_{l=1}^{P} \frac{n-l}{n} \cdot c_{n-l} \cdot a_l \quad n = 2, \ldots P$$

The cepstrum coefficients $c_1, \ldots, c_p$ are used as the p first coefficients in the Feature Vector.

Figure 3:
FIG. 3 depicts a feature vector.

Parameter of Energy Trend (PET). The energy from a number of windows are used to calculate a trend for the energy values. If the trend indicates increasing energy levels, PET is set to zero. If the trend is decreasing, the point where the trend is crossing the time-axis is calculated. A non-linear transform of this value form the PET coefficient. HBK figure The PET is added to the Feature Vector. The complete Feature Vector is thus composed according to FIG. 3.

FEATURE MAP GEOMETRY AND DEFINITIONS. Let the M map nodes be denoted $$m_i, i=0, \ldots, M-1.$$

Most often the nodes are arranged in a square (2-dimensional) grid. The distance between two map nodes i and j, is denoted $D_{i,j}$ and defined as the squared Euclidian distance ($L^2$ norm) between them $$D_{i,j}=L^2(m_i,m_j).$$

Let the input Feature Vector representing sample $x_k$ be denoted $y_k$. The map response in node i for feature k, $S_{ik}$, is defined as:

$$S_{ik} = \exp\{-d_{ik}^2/(P+1)\},$$

where the signal space distance $d_{ik}^2$ is defined as $$d_{ik}^2 = \sum_{l=1}^{P+1} w_l(y_l^k - m_l^i)^2$$

and $w_1$ is some suitable weight function.

ANNEALING FUNCTION. The task of the annealing function is to obtain an equilibrium at the end of the training. The principle is that large adjustments are allowed in the beginning of the training whereas only small (or zero) adjustments are allowed at the end. How the decrease incorporated is not critical. Linear, exponential, and even pulsating [4] decay schedules are proposed in the literature.

INITIALIZATION. Traditionally, all data driven clustering schemes, including ANNs, employ random positioning of the clusters in the signal space, by assigning (small) random numbers to the parameters. The actual values are not important as long as they are not identical. The ordering of the clusters is also at random.

TRAINING. The iterative algorithm adjust all clusters after each input Feature Vector, $y_k$, presented. The direction of the adjustment is towards $y_k$, and how much is determined partly by the annealing function, partly by the neighborhood function. The adjustment formulae for cluster $y_k$ at time instant t+1 is:

$$y_k(t+1)=y_k(t)+\gamma_{k'}(t)(z-y_k(t)),$$

where $$\gamma_{k'}(t)=f(t) \cdot g_k(t)$$

and $f(t)$ is the annealing function and $g(t)$ is the neighborhood function. Various suitable functions are discussed in [3].

EXAMPLE 3

Hard Decision A

Let 64 map nodes be arranged in an 8×8 square grid and numbered 0 to 63 from the top left to the low right corner. Thus for example the map distance $D_{0,1}=1$, $D_{0,2}=4$ and $D_{0,9}=2$.

A large database is recorded containing flow-measures from several patients during all phases of sleep. The recordings are performed at 20 Hz and stored on a memory disk. The database will contain normal sleep breathing, flow limitations, snoring, yawning, coughing, various apneic events, but also mask leakage and other artifacts.

The database is analyzed sample for sample. The 20 Hz flow-signal is first passed through an ideal differentiator. A rectangular window of 180 samples is used to form basis for extracting 4 cepstrum coefficients ($c_1, \ldots, c_4$) and the PET parameter. Thus the Feature Vector is a 5-dimensional vector with values extracted every 50 ms.

Samples are collected from the database in a random manner as long as the training proceed. The number of iterations, T, is determined by the size of the database, but as a rule of thumb, 10–30 iterations per sample may be an adequate number.

The Euclidian distance to all clusters $y_i$ i=0, …, M−1 are calculated and the cluster closest to the Feature Vector is voted winner and is denoted $y_1$.

In calculating the distance, the following weight function is employed:

$$w=[1\ 2\ 3\ 4\ 1]$$

The neighborhood function will allow all clusters to be adjusted at all times (i.e. the size of neighborhood is not decreased in time), but will penalize clusters far away from the winner $y_1$.

$$g(t)=e^{-2 \cdot D_{1i}}, \forall t$$

The annealing function, $f(t)$, follows a linear decay schedule $$f(t)=0.2 \cdot (1-t/T) t=0, \ldots, T$$

After the training phase, the map is presented with known features such as normal breathing, flow limitation signals etc. For each event the response, S, in each node of the map is calculated (see, FIG. 2).

$$S_{ik}=\exp(-d_{ik}^2/P),$$

Regions with high response for normal breathing are labeled as normal regions; regions reacting for flow-limitations are labeled as flow-limitation area and so forth.

Figure 2:
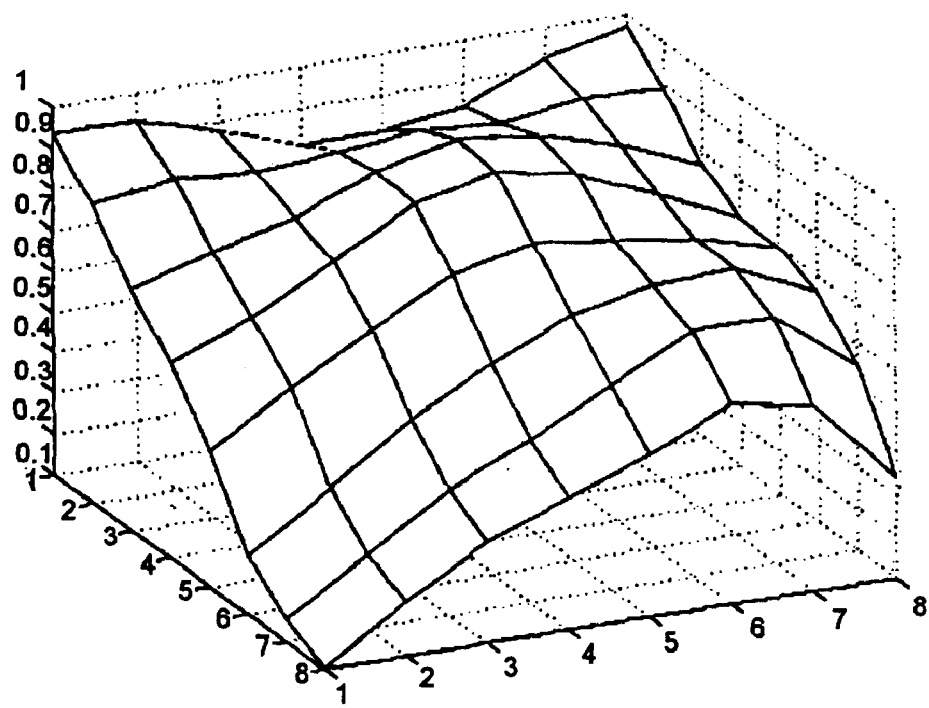
FIG. 2 depicts a feature map response in regard of example 3.

It is then decided which nodes that shall represent events needed to respond to; i.e. an alarm signal is passed to the pressure control system. In FIG. 2, the map response to an input corresponding to flow limitations is depicted. In this case, nodes X,Y,Z will probably be labeled as a flow limitation region.

EXAMPLE 4

Hard Decision B

This example is similar to the one described in example 1, but here a Hamming window of 180 samples is used instead of the rectangular. Furthermore the cepstrum coefficients are weighted to have approximately the same variances, whereas the PET parameter is given twice the variance of the cepstrum. This will give the PET parameter a little more importance than the rest of the parameters. The following weight function is employed:

$$w=[1\ 1.41\ 1.5\ 4\ 2]$$

Figure 4:
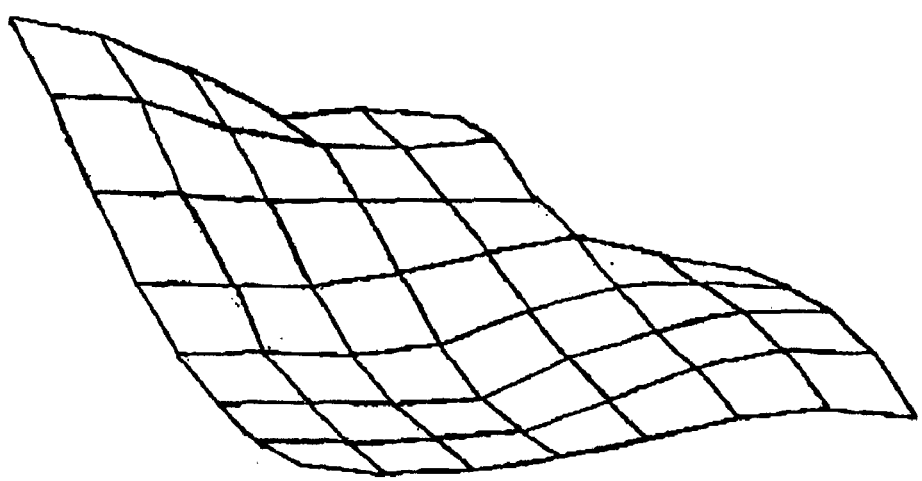
FIG. 4 depicts a feature map response in regard of example 4.

The training is carried out exactly ass before, and the map response for a typical flow-limitation signal is shown in FIG. 4. In this case, nodes X,Y,Z will probably be labeled as a flow limitation region.

EXAMPLE 5

Soft Decision

In this example, the map nodes are given a number 0, 2, 5, or 10 as labels to indicate the seriousness of the classification result. Thus instead of presenting an alarm signal on/off to the pressure control system, the number is passed on. If for instance 0 reflects normal regions and 10 reflects apnea, the numbers can be integrated to form an overall breathing status classification. If the level is very high, rapid increases in pressure is allowed, low levels allow for a pressure decrease, and intermediate levels result in a slow increase of the pressure.

EXAMPLE 6

Down Sampling

If the capacity of the processor do not allow for all calculations described above, the LPC calculation can be decimated by a factor two or four. The number of samples within the analysis window must then be reduced so that the time span of the window is still about two breathing cycles. The resolution of the map response will not suffer from this.

EXAMPLE 7

Pressure Regulation and Runtime Mode

The pressure control system will increase the pressure one step of 0.125 mbar if the ANN response is positive for 50 samples in one sequence. The pressure will decrease with one step of 0.125 mbar if the ANN response is negative for 300 samples in one sequence. The pressure will not be changed if the ANN response is changed during those sequences.

In a runtime mode, a sample of the flow signal is analyzed as described above (i.e. extracting the Feature Vector), and presented to the map, now stored in a memory bank in the APAP-unit. There is no need to calculate the exponent in the expression for map response, as the function is monotonic.

EXAMPLE 8

Program Code

```
// function ann_detect
// COPYRIGHT (TC) 2000 PePe Research
// GOTHEBORGH, SWEDEN.
#include <stdio.h>
#include "ann_detect.h"
#include "apne_func.h"
int ann_detect(const float new_sample) {
    float corr[10];
    int ana_dim = 5;
    int win = 180;
    float apol[5];
    float alpha;
    float dvec[5];
    int respx, respy;
    int resp_en, resp_ann;
    calc_corr(new_sample, win, ana_dim+1, corr);
    /* Check levels, and slope */
    resp_en = reg_r0(corr[0], &dvec[4]);
    lpc(corr, ana_dim, apol, &alpha);
    a2cep(apol, ana_dim, dvec);
    dvec [1] *= 1.41;
    dvec [2] *= 1.5;
    dvec [3] *= 4;
    dvec [4] *= 2;
    map_resp(dvec, ana_dim, &respx, &respy);
    resp_ann = apne_dec(respx, respy);
    if ( resp_ann == 1 || resp_en == 1 )
            return 1;
    return 0;
}
// functions for apne detection
//
// COPYRIGHT (C) 2000 PePe Research
// GOTHEBORGH, SWEDEN.
#define MAP_DIM_X       8
#define MAP_DIM_Y       8
#define MAP_SIZE        64
#define DATA_DIM        5
#define NHEAD           256
#define NMB_SAVE        100
#define MaxR0           180
#define MaxR0_          2 90
#define SLOPE           0.006
#include <stdio.h>
#include <math.h>
#include "map.h"
#include "annpar.h"
float distance ( const float *x const float *y int d )
{
    int i;
    float dist, t;
    t = x[0]-y[0];
    dist = t*t;
    for ( i=1; i<d; i++) {
        t = x[i]-y[i];
        dist += t*t;
    }
    return dist;
}
void calc_corr(float const rec_sample, int const win, int const ana_dim, float* corr)
{
    static float     samp_win[180];
    static int first = 0;
    static float prev_sample=0;
    float diff;
```

EXAMPLE 8-continued

Program Code

```
    int i,j;
    /* calc diff of new and prev sample */
    diff = rec_sample - prev_sample;
    prev_sample = rec_sample;
    /* Insert new sample first, move all the other */
    for ( i=win-1; i > 0; i-- ) {
        samp_win[i] = samp_win[i-1];
    }
    samp_win[0] = diff;
    for( j = 0; j < ana_dim; j++){
        corr[j] = 0;
        for (i = 0; i < win-j; i++){
            corr[j] += samp_win[i]*samp_win[i+j];
        }
    }
    /* Add an offset to avoid near /0 operations */
    corr[0] +=1;
}
int reg_r0(float cur_r0)
{
    static float rf[MaxR0];
    static int first = 1;
    static int index = 0;
    int i;
    static float prev_r0 = 0;
    float k,m, rf0, dec;
    rf0 = 0.9*prev_r0 + 0.1*cur_r0;
    prev_r0 = rf0;
    k = 0.5*(rf0 - rf[MaxR0-1]);
    m = (rf0 + rf[MaxR0/2] + rf[MaxR0-1])/3.;
    /*update the saved old values */
    for ( i=MaxR0-1; i > 0; i-- ) {
        rf[i] = rf[i-1];
    }
    rf[0] = rf0;
    /* second rule check the regression line */
    if (k > -1)
        dec = 1000;
    else
        dec = -MaxR0_2*((m/k)+1);
    *out = exp(-SLOPE*dec);
    /* first rule, if energy less then 15 make alarm */
    if (cur_r0 < 15 ){
        return 1;
    }
    /* second rule, if regression line crosses zero line too soon make alarm */
    if ( dec < 50 ){
        return 1;
    }
    return 0;
}
void lpc(float* const acf, int const ana_dim, float* aCoeffs, float* alpha)
{
    float err;
    int i, j;
    float refls[5];
    float sum, refl, tmp;
    err = acf[0];
    for (i = 0; i < ana_dim; i++) {
        if (err <= 0) {
            refls[i] = 0;
            aCoeffs[i] = 0;
        } else {
            sum = 0;
            for (j = 0; j < i; j++)
                sum += aCoeffs[j] * acf[i - j];
            refl = (acf[i + 1] - sum) / err;
            refls[i] = refl;
            for (j = 0; j < i / 2; j++) {
                tmp = aCoeffs[j];
                aCoeffs[j] -= refl * aCoeffs[i - j - 1];
                aCoeffs [i - j - 1] -= refl * tmp;
            }
            if (i & 1)
                aCoeffs[i / 2] -=refl * aCoeffs[i / 2];
            aCoeffs[i] = refl;
            err *= i - refl * refl;
        }
    }
    for (i = 0; i < ana_dim; i++) {
        aCoefs[i] = -aCoeffs[i];
    }
    *alpha = sqrt(err);
}
void a2cep(float* const a, int const ana_dim, float* cep)
{
    int l, j, ind;
    float sum;
    cep [0]= -1*a[0];
    for (l = 2; l < ana_dim+1; l++) {
        sum = l*a[l-1];
        for (j=2; j <= l; j++) {
            ind = l-j+1;
            sum = sum + a[j-2]*cep[ind-1]*ind;
        }
        cep[l-1] = -sum/l;
    }
}
void map_resp(float* const dvec, int const ana_dim, int* respx, int* respy)
{
    int xm, ym, ind, i;
    float dist;
    float min_dist = 1000000;
    for( xm = 0; xm < MAP_DIM_X; xm ++ ) {
        for( ym = 0; ym < MAP_DIM_Y; ym ++ ) {
            ind = (xm + (ym*MAP_DIM_X))*DATA_DIM;
            if ((dist = distance(dvec, &map[ind], DATA_DIM)) < min_dist ){
                *respx = xm;
                *respy = ym;
                min_dist = dist;
            }
        }
    }
}
int apne_dec( int const respx, int const respy, float* d_out)
{
    static float mean_x = MAP_DIM_X/2;
    static float mean_y = MAP_DIM_Y/2;
    static int first = 0;
    static float resp_hist[NMB_SAVE];
    static int n_hist_x = 0;
    static int n_hist_y = 0;
    float rad_filt;
    float rad_inst;
    double dx, dy, dfx, dfy;
        int current_in_area = 0;
    int new_in = 0, i;
    dx = (respx-area_x_mid )*( respx-area_x_mid);
    dy = (respy-area_y_mid )*( respy-area_y_mid);
    rad_inst = sqrt(dx + dy);
    mean_x = lp_a*mean_x + (1-lp_a)*respx;
    mean_y = lp_a*mean_y + (1-lp_a)*respy;
    dfx = (mean_x-x_cen)*(mean_x-x_cen);
    dfy = (mean_y-y_cen)*(mean_y-y_cen);
    rad_filt = sqrt(dfx +dfy);
    /*check if the current response is in the area */
    if ( area_rad > rad_inst) new_in = 1;
    for( i = NMB_SAVE-1; i> 0; i-- ) {
        resp_hist[i] = resp_hist[i-1];
    }
    resp_hist[0] = new_in;
    for( i = 0; i < nb_resp_hist; i++ ) {
        if( 1 == resp_hist[i] ) current_in_area++;
    }
    if ( mean_x > det_x_min &&
        mean_y > det_y_min &&
        mean_x < det_x_max &&
        mean_y < det_y_max)
        /* standard case, when detecting a simple square area of the filtred response */
```

EXAMPLE 8-continued

```
Program Code return 0;
    else if (rad > rad_filt )
        /* within circle calc, otherwise same as above */
        return 0;
    else if (resp_in_area < current_in_area )
        /*instant resp totaly over the given number */
        return 0;
    else
        return 1;
};
```

EXAMPLE 9

Patient Treatment

Equipment. Breas CPAP pv10 prototype (Breas AB, Mölndal, Sweden) with internal flow measurement; PSG system, EMBLA™ Polysomnography (Embla hf, Reykjavik, Iceland); PC with artificial neural network software for sleep disturbance detection. Patients. 6 males aged from 31 to 60 years, suffering from sleep disorders of various kind.

Measurement. The patient was set up with all sensors from the PSG system: EEG, EOG, EMG, oxygen saturation, pulse, nasal flow thermistor measurement, body position. With this setup it is possible to determine sleep stages, arousals, sleep apnea, sleep hypoapnea, and other sleep related events. The CPAP provides air through a tube via a nasal mask to the patient. Via the CPAP communication interface the PC was connected to the CPAP. The PC software can read air flow values from the CPAP and set new pressure set points on the CPAP by the communication interface. The information was exchanged at a rate of about 20 Hz. The PC program feeds the flow values into the artificial neural network (ANN). The output from the ANN is entered into a pressure regulation algorithm (PRA). The pressure regulation algorithm calculates a new pressure set point and activates the new value in the CPAP. The output from the artificial neural network and the pressure setpoint is read by the PSG system.

Evaluation. In a normal CPAP titration (sleep disorder analysis) a CPAP is connected to a patient during sleep. The CPAP pressure is adjusted during the night so as to put the patient in a state with no indications of sleep disorders. This pressure is the one used in the CPAP treatment. The patient's need for various CPAP pressures can be seen with the PSG system breath-by-breath. The required CPAP pressure varies depending on sleep stage, body position, etc. The data from the auto CPAP test was evaluated in the PSG system in the same manner as for CPAP titration by a physician used to evaluate patients receiving CPAP treatment. Thereby the correlation between the detection of sleep disorder by the ANN and the analysis in the PSG system could be determined. The good correlation obtained indicated that the AFN reacted correctly.

References

[1] T. Kohonen, T. Torkkola, M. Shozakai, O. Ventä "Phonetic typewriter for Finnish and Japanese", Proc IEEE ICASSP, New York, N.Y., 1988

[2] H. C. Leung, V. W. Zue "Some Phonetic Recognition Experiments using Artificial Neural Nets"., Proc IEEE ICASSP, New York, N.Y., 1988

[3] P. Brauer "Infrastructure in Kohonen maps", Proc. IEEE ICASSP, Glasgow, Scotland, 1989.

[4] P. Knagenhjelm "A Recursive Design Method for Robust Vector Quantization", Proc. ICSPAT, Boston, Mass., 1992.

What is claimed is:

1. A method for the detection and treatment of disordered breathing during sleep employing an artificial neural network (ANN) in which data related to breathing gas flow are analyzed, comprising:

placing a mask with a tube over a patient's airway, the mask being in communication with a source of a pressurized breathing gas controlled by a continuous positive airway pressure (CPAP) system, thereby establishing a respiratory circuit;

periodically sampling the gas flow in the circuit;

performing a linear predictive coding (LPC) multiple parameter analysis for each sample to provide thereby respective A-parameters;

converting said A-parameters into cepstrum parameters;

processing said cepstrum parameters using an ANN trained to recognize breathing patterns characteristic of sleep disordered breathing; and controlling a breathing gas pressure in response to an output of said ANN.

2. The method of claim 1, where in said parameter values are fed to the network at a frequency of from 2 Hz to 30 Hz.

3. The method of claim 2, wherein said parameter values are fed to the network at a frequency of shout 20 Hz.

4. The method of claim 1, wherein said parameters comprise cepstrum coefficients, energy slope, difference in trend.

5. The method of claim 1, wherein the ANN has been trained with data collected from a large number of patients.

6. The method of claim 1, wherein the ANN has been trained with data collected from patients during a particular stage of sleep.

7. The method of claim 1, wherein the ANN has been trained with data collected from patients resting in a particular body position during sleep.

8. The method of claim 1, wherein the ANN has been trained with data collected from patients being under influence of drugs including alcohol during sleep.

9. The method of claim 1, wherein the ANN has been trained with data collected from patients by use of a polysomnography system.

10. The method of claim 1, wherein the ANN comprises a number of nodes representing sets of training data.

11. The method of claim 1, wherein the ANN is a Kohonen map ANN.

12. The method of claim 11, comprising a structure of data stored in a non-volatile memory.

13. The method of claim 12, wherein the non-volatile memory is comprised by an auto CPAP.

14. The method of claim 11, wherein the ANN comprises areas representing initial stages of apnea.

15. The method of claim 14, wherein a closed trajectory characteristic of the breathing pattern of the patent is made to pass through the ANN and is analyzed in regard of its geometric relationship to said areas representing initial stages of apnea, the passage of said trajectory through such area or touching such area being indicative of a disturbed breathing pattern and being used to control the ACPAP so as to increase the amount of air provided to the patient to restore normal breathing.

16. The method of claim 15, wherein the additional amount of air adduced to restore normal breathing is reduced upon a normal breathing pattern having been re-established.

17. The method of claim 11, comprising the use of linear predictive coding to analyze the parameter values fed to the ANN.

18. The method of claim 17, wherein, in said linear predictive coding analysis, so-called A-parameters from the analysis are converted to cepstrum parameters for optimal correlation between parameter distance and conceptual distance.

19. The method of claim 11, wherein prediction error in calculating linear predictive coding is used as a basis for determining the parameter value next in line.

20. The method of claim 19, wherein said prediction error is filtered to counteract short-term variations, and is normalized with the total energy of the analytical window.

21. A method of treating sleep disorder breathing, the method comprising the steps of:

placing an interface over a patient's airway, the interface coupled to a source of pressurized gas;

measuring a respiration-related variable in the interface to derive therefrom corresponding cepstrum parameters;

providing said cepstrum data to an artificial neural network trained to recognize patterns characterizing sleep disorder breathing; and responsive to recognition by the artificial neural network of sleep disorder breathing, supplying pressurized gas to the patient's airway through the interface.

22. The method according to claim 21 further comprising the step of:

comparing a number of outputs of the artificial neural network over a selected interval to a selected threshold value and indicating sleep disorder breathing only if the number of outputs of the artificial neural network indicative of sleep disorder breathing exceeds the selected threshold value.

23. The method according to claim 21 further comprising the step of normalizing the measured respiration-related variable prior to providing them to the artificial neural network.

24. The method according to claim 21 wherein the respiration-related variable is the pressure in the interlace.

25. A method of treating sleep disorder breathing, the method comprising the steps of:

placing an interface over a patient's airway, the interface coupled to a source of pressurized gas;

periodically sampling pressure in the interface;

periodically inputting cepstrum data from the sample of pressure in the interface into an artificial neural network trained to recognize patterns characterizing sleep disorder breathing, the artificial neural network producing an output for each sample of pressure input;

comparing the number of outputs indicating sleep disorder breathing to a selected threshold value, sleep disorder breathing being indicated if the number of outputs exceeds the threshold value; and responsive indicated sleep disorder breathing, supplying pressurized gas to the patient's airway through the interface.

26. The method according to claim 25 further including the step of obtaining a frequency spectrum from the measured respiration-related variables.

27. The method according to claim 26 further comprising the step of:

normalizing the components of the frequency spectrum prior to inputting them into the artificial neural network.

28. An apparatus for treatment of sleep disorder breathing comprising:

an interface for placement over a patient's airway, the interface coupled to a source of pressurized gas;

means for measuring respiration-related variables in the interface;

means for inputting cepstrum data from the respiration-related variables into an artificial neural network trained to recognize patterns characterizing sleep disorder breathing;

means for supplying pressurized gas to the patient's airway through the interface responsive to recognition by the artificial neural network of sleep disorder breathing.

29. The apparatus according to claim 28 further comprising:

means for obtaining a frequency spectrum from the measured respiration-related variables.

30. The apparatus according to claim 28 further comprising:

means for comparing a number of outputs of the artificial neural network over a selected interval to a selected threshold value and indicating sleep disorder breathing only if the number of outputs of the artificial neural network indicative of sleep disorder breathing exceeds the selected threshold value.

31. The apparatus according to claim 28 further comprising:

means for normalizing the measured respiration-related variables prior to inputting them into the artificial neural network.

* * * * *

UNITED STATES PATENT AND TRADEMARK OFFICE
CERTIFICATE OF CORRECTION

PATENT NO. : 6,889,691 B2
DATED : May 10, 2005
INVENTOR(S) : Ove Eklund et al.

It is certified that error appears in the above-identified patent and that said Letters Patent is hereby corrected as shown below:

Column 14,
Line 29, "shout" should be -- about --.
Line 58, "patent" should be -- patient --.

Column 15,
Line 40, "interlace" should be -- interface --.

Signed and Sealed this

Second Day of August, 2005

JON W. DUDAS
*Director of the United States Patent and Trademark Office*